United States Patent [19]

Tateno et al.

[11] Patent Number: 5,430,184
[45] Date of Patent: Jul. 4, 1995

[54] PROCESS FOR PREPARING 1,4-CYCLOHEXANDICARBOXYLIC ACID

[75] Inventors: Yoshiaki Tateno; Chihaya Sano; Kotone Tanaka; Mitsuo Magara, all of Shizuoka; Naoki Okamoto, Chiba; Kazuaki Kato, Saitama, all of Japan

[73] Assignee: Towa Chemical Industry Co., Ltd., Tokyo, Japan

[21] Appl. No.: 169,132

[22] Filed: Dec. 17, 1993

[30] Foreign Application Priority Data

Dec. 21, 1992 [JP] Japan .................. 4-355391

[51] Int. Cl.⁶ .................................. C07C 61/09
[52] U.S. Cl. ........................................ 562/509
[58] Field of Search ............................. 562/509

[56] References Cited

U.S. PATENT DOCUMENTS

| | | | |
|---|---|---|---|
| 2,675,390 | 4/1954 | Rosenblatt | 562/509 |
| 2,828,335 | 3/1958 | Fertandig | 562/509 |
| 2,888,484 | 5/1959 | Dehm | 562/509 |
| 3,326,972 | 6/1967 | Schenk | 562/509 |
| 3,444,237 | 5/1969 | Jaffe | 562/509 |
| 3,607,917 | 9/1971 | Buls | 562/509 |
| 3,607,926 | 9/1971 | Smetana | 260/533 |
| 3,957,947 | 5/1976 | Yamada | 423/111 |
| 4,592,784 | 6/1986 | Ghizzi | 134/15 |
| 4,754,064 | 6/1988 | Lillwitz | 562/509 |
| 5,118,841 | 6/1992 | Cook | 562/509 |
| 5,159,109 | 10/1992 | Rosen | 562/509 |
| 5,202,475 | 4/1993 | Cook | 562/509 |

*Primary Examiner*—Michael L. Shippen
*Attorney, Agent, or Firm*—Beveridge, DeGrandi, Weilacher & Young

[57] ABSTRACT

An economic hydrogenation process is provided which significantly suppresses palladium catalyzer activity loss, for obtaining very high purity 1,4-CHDA through a simple operation. The process includes bringing the solution containing the hydrogenation reaction product of interest into contact with steam. The resultant products may include resins having excellent weather resistance or physical properties or high purity medical drugs. The process for preparing 1,4-cyclohexandicarboxylic acid is characterized by two consecutive steps. The first step includes the hydrogenation of a solution containing terephthalic acid in the presence of a palladium catalyzer in an acid resistant vessel or in a vessel layered with acid resistant material for preparing 1,4-cyclohexandicarboxylic acid. The second step includes contacting the solution containing 1,4-cyclohexandicarboxylic acid obtained in the first step with the steam, and extracting impurities moved to the steam.

17 Claims, 2 Drawing Sheets

PROCESS FOR PREPARING 1,4-CYCLOHEXANDICARBOXYLIC ACID

1. TITLE OF THE INVENTION

Process for preparing 1,4-cyclohexandicarboxylic acid

2. Field of the Invention

The present invention relates to a process for preparing 1,4-cyclohexandicarboxylic acid (hereinafter may be referred to as "1,4-CHDA").

3. Background of the Invention 1,4-CHDA is useful as raw material for medical drugs, synthetic resins, synthetic fibers, paint, etc., and to be more specific, it is used as raw material for producing resins and fibers having excellent heat resistance, weather resistance and physical strength, etc.

Among methods for preparing 1,4-CHDA, one representative process consists in obtaining 1,4-CHDA through hydrogenation of benzene ring by using high purity terephthalic acid (hereinafter may be referred to as "TPA") among those produced as industrial raw materials. A plurality of processes have already been disclosed.

These processes may be generally classified into those where benzene is reduced after having once obtained metal salts, such as sodium and the like, or various esters from the acid part of TPA, and those processes where benzene is reduced directly from the acid.

As the former process needs supplementary steps for leaving the raw material TPA as a derivative, e.g., reducing before rendering it to the acid form, the direct reduction process is more economic and has been believed to be more promising.

Among a number of trials, few have succeeded in reducing the acid as it is, including, for instance, the process disclosed in (1) Japanese TOKKYO-KOKOKU-KOHO (Publication for Opposition of Examined Patent Application) SHOWA 36(1961)-522, wherein TPA with aqueous medium is hydrogenated under the conditions of 150° to 300° C. and about 210 kg/cm² in a stainless pressure vessel using palladium or ruthenium as a catalyzer. The reaction product is dissolved in alkali, such as sodium hydroxide, and the catalyzer is filtered before adding acid for neutralization and acid dipping, to obtain 1,4-CHDA of interest.

On the other hand, the process disclosed in (2) Journal of Organic Chemistry, 31(10) pp. 3438-9 (1966) comprises the steps of hydrogenating TPA in aqueous medium with rhodium on alumina as a catalyzer at 60° to 70° C. and with a hydrogen pressure of less than 3 times atmospheric pressure. The catalyzer is removed by high temperature filtering, and 1,4-CHDA of interest is extracted with chloroform by a yield of approximately 90%.

Moreover, another process is disclosed in (3) Japanese TOKKYO-KOKAI-KOHO (18-month Publication of Unexamined Patent Application) SHOWA 58(1983)-198439, wherein TPA with aqueous medium is hydrogenated under the conditions of 150° C. and about 100 kg/cm² in a stainless steel pressure vessel using palladium or ruthenium as a catalyzer, which are then separated under a specific temperature condition within the range of 110° to 180° C. and defined as $t > = 43.5 \times \log_{10} C + 69.5$ (wherein t=degrees Celsius, and C=amount of 1,4-CHDA dissolved to 100 weight parts of water, expressed by weight part), to obtain 1,4-CHDA of interest.

Recently, there has been a demand for products having an international competitive power and high level functions in the field of medical drugs or the field of resins where 1,4-CHDA is used as a raw material. Thus, it is required that the raw material for producing 1,4-CHDA be of extremely low impurity, so as to offer an international cost competitive power, while producing a high purity product of which 1,4-CHDA purity is approximately 99.9 weight %. The product should contain low amounts of minerals like chlorine or other impurities, such as affinities of cyclohexancarboxylic acid, and this product should be supplied without a significant rise in price.

1,4-CHDA obtained by the conventional processes, however, was not pure enough to satisfy such a high level quality demand, and even if some special preparation method could be considered, it would remain unpractical because it would require an extremely complicated and expensive process.

For instance, when followed up, the process (1) above presents difficulties such as a dramatic loss of catalyzer activity which is necessary for the reduction, and, in consequence, this process has an extremely high catalyzer cost.

Additionally, a fateful problem remained unresolved, namely, it has been impossible to prevent impurities from being mixed in 1,4-CHDA. Such impurities include 4-methylcyclohexancarboxylic acid and other affinities of cyclohexancarboxylic acid, byproducts of the reaction, sodium sulfate, sodium chloride and other minerals produced by the acid for recovering 1,4-CHDA from alkali used for dissolving the raw material, TPA, or from reaction products of the hydrogenation.

In consequence, irregular reactions may be caused by the impurities contained in the raw material during the polymerization of resin or others using 1,4-CHDA obtained by this process as a raw material. Additionally, the heat resistance, the physical strength or the weather resistance of the final product, such as a resin, may be significantly deteriorated by the impurities contained in the raw material. The improvement of these disadvantages remains unresolved.

In the process (2) above, like the above-mentioned process (1), although the price is ten times higher for rhodium than palladium or ruthenium, the catalyzer life of rhodium used as the catalyzer is not longer in proportion to the price, the purity of the product of interest in the reaction product is as low as approximately 95% and, moreover, it has been impossible to prevent impurities, such as affinities of cyclohexancarboxylic acid, and reaction byproducts, from being mixed in with the 1,4-CHDA.

Additionally, chloroform used as an extraction medium in the preparation according to this process also dissolves the above-mentioned impurities, so, in consequence, the resulting purity of 1,4-CHDA is not significantly different from the purity before the extraction. Moreover, as this medium itself is a poison, its use is not preferable, and the use of a medium other than water requires additional cost for equipment and for extraction of the medium. The improvement of these difficulties has also been left unresolved.

While in the process (3) above, although exempt from sodium sulfate, sodium chloride and other minerals produced from alkalis and acids, and affinities of cyclohexancarboxylic acid are produced as byproducts of the hydrogenation in which palladium or ruthenium is used as the catalyzer at 110° to 180° C. and it has been impossible to prevent these impurities from being mixed in with the 1,4-CHDA.

As a means to resolve these problems, it would be possible to crystallize the product containing 1,4-CHDA. However, as 1,4-CHDA and the impurities are extremely insoluble in the water, it is impossible to obtain a high purity product having a purity of at least 99.9%, by crystallizing 1,4-CHDA of which the purity is less than 99.5%, when the crystallization is undertaken from water.

On the other hand, a high temperature and/or a high pressure are required so as not to leave some raw material non reduced during the repeated use of the catalyzer, but 1,4-CHDA purity of the reaction product decreases because of such a severe temperature condition. This disadvantage also has not been resolved.

In the preparation processes of 1,4-CHDA described above, the example of preparation using new catalyzer which is not deprived of activity is disclosed, and it seems apparent that they would permit production of 1,4-CHDA of relatively high purity. The inventors have, however, followed up these processes and found that 1,4-CHDA of low purity is produced in almost any of them, and the product could not be used in the resultant form.

The reason seems to be as follows: in many cases, impurities are produced but absorbed preferentially by the absorption points, such as active carbon used as a catalyzer carrier. In consequence, though the apparent 1,4-CHDA purity is relatively high, as the absorption capacity of active carbon and other adsorption points are limited, the impurities could be detected at the rate they are produced in reality, once the absorption capacity has been attained.

On the other hand, a stainless steel pressure vessel is adopted for the conventional preparation methods, but the inventors have made detailed research on a conventional stainless steel vessel by introducing solutions of TPA or 1,4-CHDA therein and making contact with the vessel wall at a temperature at which the hydrogenation will take place. In this research, it was found that nickel, iron, chrome, molybdenum and other components of the stainless steel are dissolved in the solution and, acting as catalytic poison, significantly lower the catalyzer activity.

Given these restrictions, the conventional processes can not allow economical production due to rapid decrease of catalyzer activity, and the reaction product can not meet recent severe requirements, because the conventional reaction produces more impurities than the expectation during the preparation of 1,4-CHDA. Moreover, it is difficult to improve the purity of 1,4-CHDA through the conventional processes. Therefore, the development of a method that could resolve the various problems mentioned above has been awaited eagerly.

4. Disclosure of the Invention

The inventors have made a study on the behavior of TPA and its alkali salt against various reactions, and have examined actively the realization of an economical process and method for improving the product purity. In this study, it was found that the drop of catalyzer activity is provoked by nickel, chromium, molybdenum, iron and others dissolved from the wall of a metal pressure vessel made, for instance, of stainless steel which is conventionally used. Furthermore, the inventors have succeeded in realizing an economical hydrogenation with a remarkable suppression of the drop of catalyzer activity through the adoption of a vessel providing a high acid resistance or a vessel provided with a layer of acid resistant material as a reactor, and, moreover, they have succeeded in obtaining extremely high purity 1,4-CHDA by bringing the solution containing hydrogenation product into contact with the steam.

Now the content of the present invention will be described in detail.

First, the present invention is a process for preparing 1,4-cyclohexandicarboxylic acid characterized by passing consecutively through a first step and a second step, wherein the first step comprises the hydrogenation of TPA containing solution in the presence of a palladium catalyzer in an acid resistant vessel or in a vessel layered with acid resistant material to thereby prepare 1,4-cyclohexandicarboxylic acid solution. The second step comprises contacting the solution containing 1,4-cyclohexandicarboxylic acid obtained in the first step with steam, and extracting impurities moved to the steam.

Second, the present invention is a process for preparing 1,4-cyclohexandicarboxylic acid, wherein the hydrogenation of the first step is performed under a hydrogen pressure between 2 kg/cm$^2$ and less than 10 kg/cm$^2$.

Third, the present invention is a process for preparing 1,4-cyclohexandicarboxylic acid, wherein the hydrogenation of the first step is performed in a pressure vessel provided with a vitreous layer.

Fourth, the present invention is a process for preparing 1,4-cyclohexandicarboxylic acid wherein, in the second step, 1,4-cyclohexandicarboxylic acid is brought continuously into contact in counterflow with steam by continuously supplying solution containing 1,4-cyclohexandicarboxylic acid to a first end of a packed tower, supplying steam continuously to a second end of the packed tower, evacuating 1,4-cyclohexandicarboxylic acid discontinuously or continuously from the second end of the packed tower, evacuating steam from the first end of the packed tower, and removing impurities moved to the steam by condensing the steam or by passing the steam through an alkaline aqueous solution. The steam may be heated and recycled.

As for the quality of TPA used for the present invention, saying nothing of high purity products that have been used conventionally as raw material for preparing 1,4-CHDA, materials of general industrial use quality (which have not been used conventionally because of their slightly lower purity) can be adopted advantageously; however, it is preferable that they contain low metal ions content which would act as a catalyzer poison during the hydrogenation reaction.

Additionally, the preferable TPA concentration for the embodiment of the present invention is 5 to 50% for the first step; however, a more preferable concentration is 10 to 40%.

In the embodiment of the present invention, a concentration higher or lower than the above-mentioned concentration range of the first step is not preferable, because the production will not be as effective as the equipment scale if it is lower than 5%, and because the handling will be difficult due to poor solubility of the trans-isomer if it is higher than 50%.

As a catalyzer for the hydrogenation reaction used advantageously in the present invention, metal palladium carried on a catalyst support can be adopted advantageously, and as the catalyst support, carbon represented by various activated charcoals is most preferable among alumina, silica or carbon because it is hardly affected by acid.

The palladium amount adopted advantageously for the embodiment of the present invention is 2 to 20%, expressed by the rate of metal palladium content in the catalyzer weight. 5 to 10% palladium content is more preferable.

In the embodiment of the present invention, various alcohols, water or 1,4-CHDA can be used as a medium for controlling the concentration; however, water is most preferable because it is inert to the reaction and the price is low.

Concerning acid resistant materials and acid resistant vessels, high acid resistant metals such as hastelloy steel, inconel steel and their compacts, or non metallic high acid resistant materials, such as ceramics, enamel, glass or other vitreous material or their compacts can be used. However, vessels made of iron or stainless steel used for an ordinary pressure vessel and provided with a lining of various acid resistant materials mentioned hereinabove are economic and can also be adopted advantageously.

The parameters for an advantageous embodiment of the first step of the present invention includes the temperature of 120° to 160° C., a hydrogen pressure of 1 to 50 kg/cm$^2$ (or more preferably between 2 kg/cm$^2$ and less than 10 kg/cm$^2$), and a reaction time of 30 to 120 minutes, and deviation from this range is not desirable in any case because the yield and the purity of the product will be affected adversely.

As for the concentration of the reaction product containing 1,4-CHDA used for the second step, it is most economic to use the concentration of the filtrate as it is after the removal of catalyzer following the hydrogenation; however, given the rate of cis- and trans-1,4-CHDA usually obtained, economic restrictions and the solubility into the water, the concentration range of approximately 2% to 40% is preferable, and the range from 5% to 30% is most preferable.

Moreover, there is no specific restriction as for the proportion of cis- and trans-1,4-CHDA contained in the reaction product containing 1,4-CHDA; however, the dissolution temperature of the reaction product in water generally tends to increase as the proportion of trans-1,4-CHDA increases, and a proportion of cis-: trans-1,4-CHDA=approximately 80:20 to 50:50 is suitable for the operation.

There is also no particular restriction for the steam used in the second step of the present invention, and steam produced by an ordinary steam generator is satisfactory provided that it meets the temperature requirement of the embodiment of the present invention.

In the second step, solution containing 1,4-cyclohexandicarboxylic acid is brought into contact with steam by batch or continuously, and both methods may be adopted for the present invention, although the continuous method is more efficient.

On the other hand, the method of removing impurities moved to the steam side after the contact of 1,4-CHDA with the steam may also be carried out both by batch or continuously, and it can be performed by removing the mixture of impurities and steam by means of condensation of the steam, by injecting the steam into an alkaline aqueous solution or by introducing the steam into a shower of alkaline aqueous solution.

Moreover, as a preferable embodiment of the second step of the present invention, the solution containing 1,4-cyclohexandicarboxylic acid and steam may be brought into contact in counterflow.

Steam may be recycled in order to reduce the energy loss throughout the process and, as mentioned above, after having removed impurities by means of an alkaline aqueous solution, the steam may be heated as necessary for reuse.

The above-mentioned respective operations of the second step may certainly be combined, however, among such combinations, the method comprising the steps of bringing solution containing 1,4-CHDA and steam into contact in counterflow, and bringing steam containing impurities into contact with alkaline aqueous solution in order to absorb impurities by the alkaline aqueous solution before reusing the steam is most advantageous from the economic point of view.

Now the method will be described in more detail. First, a tower (A) and a tower (B), filled with a charge such as Raschig rings, are provided, then an upper portion of the tower (A) and a lower portion of the tower (B), and a lower portion of the tower (A) and an upper portion of the tower (B) are connected respectively through piping. Each of the pipings and towers is provided with a structure, such as jacket, etc., that would allow adjustment of the predetermined temperature. A pump 9 is provided having a function of circulating the steam in the middle of the piping connecting the lower portion of tower (A) and the upper portion of tower (B), positioning the tower (A) at the evacuation side.

Next, operating the pump 9 of the equipment, heated solution containing 1,4-CHDA is introduced continuously at the upper portion of tower (A) and evacuated from the lower portion of tower (A), and at the same time, heated alkaline aqueous solution is introduced continuously at the upper portion of tower (B) and evacuated from the lower portion of tower (B).

At this time, the preferable concentration of the solution containing 1,4-CHDA supplied to tower (A) is 2 to 40% but 5 to 30% is more preferable.

On the other hand, the preferable concentration of the alkaline aqueous solution supplied to tower (B) is 1 to 50%, but 1 to 20% is more preferable.

The preferable flow rate of the solution containing 1,4-CHDA supplied to tower (A) is about 1 to 6 times the capacity of tower (A) per hour, depending on its concentration, temperature or the content of impurities contained therein.

Here, a flow rate of 1,4-CHDA less than 1 times the capacity per hour is not preferable because it lowers the efficiency of production unnecessarily, and a flow rate more than 6 times the capacity per hour is also undesirable because the removal of impurities may become imperfect.

Moreover, the preferable flow rate of the alkaline aqueous solution supplied to tower (B) is about 1 to 6 times the capacity of tower (B), and a flow rate superior or inferior to this range is, in both case, undesirable because alkali may become excessive or insufficient.

As for the alkali in this invention, sodium hydroxide, potassium hydroxide or sodium triphosphate may be used advantageously, but among various other alkalis, salts of calcium often provoke scale, and carbonates generate gas; therefore, they are not recommended, although they can be used.

The preferable steam circulation rate by the pump 9 is approximately 0.1 to 1.6 times the tower (A) capacity per hour when it is converted to the volume of steam condensed water, and any deviation from this range at either end may affect adversely the cost or yield of the second step, and, therefore, is not desirable.

When the second step of the above-mentioned method is adopted, it is recommended to keep the temperature of the respective tower and piping within 100° to 150° C., or more preferably within 102° to 130° C., and a difference in temperature of tower (A) and tower (B) is not undesirable because the supplied solution containing 1,4-CHDA may boil or the steam may condense in a way to imbalance the mass balance. A temperature inferior to 100° C. may provoke insufficient removal of impurities, and a temperature exceeding 150° C. is also undesirable because it may decrease the yield due to the decomposition, etc.

In tower (B), the velocity with which impurities contained in the steam are absorbed and move toward the alkali side is so rapid, a method wherein the steam containing impurities coming from the upper portion of tower (A) is brought into contact with a shower-form of alkaline aqueous solution, or a method wherein the steam is blown directly into the alkaline aqueous solution, may be adopted.

As described hereinabove, the embodiment of the present invention permits suppression of the activity drop of the hydrogenation catalyzer, to assure a long catalyzer life. This permits realization of an economic method for obtaining 1,4-CHDA by subjecting TPA directly to the hydrogenation reaction, and, moreover, 1,4-CHDA of high quality is prepared that will meet with the actual severe requirements.

The embodiment of the present invention permits realization of an economical hydrogenation reaction through a significant suppression of the catalyzer activity loss of expensive palladium, to thereby obtain extremely high purity 1,4-CHDA with very simple operations by bringing the solution containing the hydrogenation product into contact with steam. In this manner, resins are produced showing excellent weather resistance or physical strength or high purity medical drugs.

5. BRIEF DESCRIPTION OF THE DRAWINGS

Figure 1:
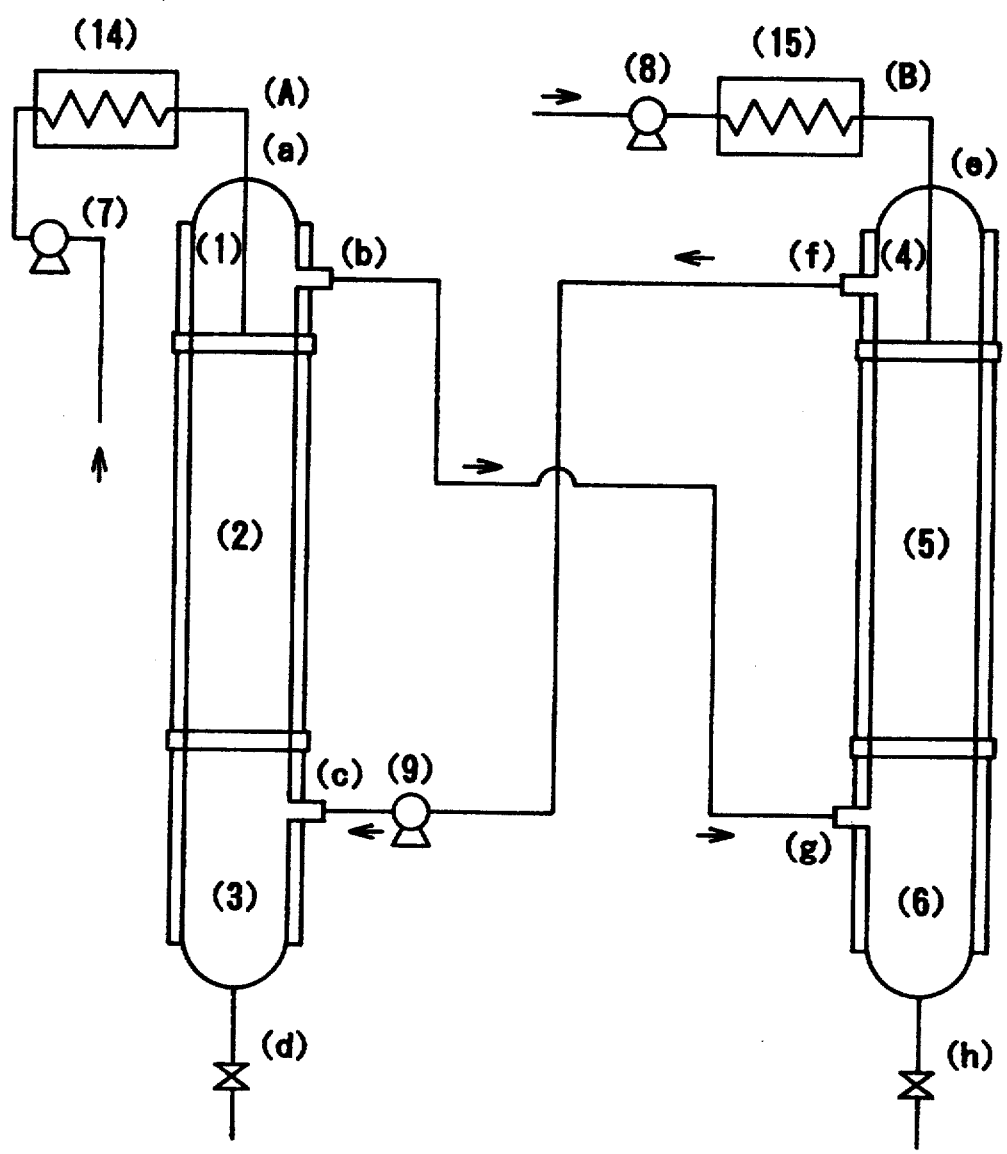
FIG. 1 is a schematic diagram for the first Example of the equipment provided with a heating jacket to be used for an embodiment of the present invention.

Reference numbers used in the drawings represent the following parts, respectively: A: Tower, B: Tower, C: Tower, a: Inlet, b: Steam outlet, c: Steam inlet, d: Outlet, e: Alkaline liquid inlet, f: Steam outlet, g: Steam inlet, h: Alkaline liquid outlet, i: Alkaline liquid inlet, j: Steam outlet, k: Alkaline liquid outlet, m: Steam inlet, 1: Vessel, 2: Column, 3: Liquid receiving vessel, 4: Vessel, 5: Column, 6: Liquid receiving vessel, 7: Pump, 8: Pump, 9: Steam circulation pump, 10: Vessel, 11: Alkaline shower equipment, 12: Liquid receiving vessel, 13: Pump, 14: Preheater, and 15: Preheater.

6. PREFERRED EMBODIMENTS

Now the present invention will be illustrated more specifically by the following reference examples and embodiment examples referring to the attached drawings. However, these examples are not intended to limit the scope of the present invention.

[Embodiment example 1] (First step)

30 g of terephthalic acid, 270 g of water and 8 g of 10% palladium-carbon catalyzer (supplied by N. E. Chemcat Corporation) are introduced into a glass autoclave of 500 ml provided with agitator blades made of fluororesin (Teflon ®, polytetrafluoroethylene produced by the E. I. DuPont de Nemours Co.) and hydrogenated at 130° C. under a hydrogen pressure of 8.3 to 9.8 kg/cm$^2$, and the reaction stops after 50 minutes when the hydrogen absorption is no longer observed.

The reaction liquid is evacuated from the autoclave, all the catalyzer is filtered off for recovering, and the recovered catalyzer is washed with 2000 ml of boiling water before adding it to the filtrate.

The filtrate is then analyzed by gas-liquid chromatography, and the 1,4-CHDA purity in the solid component is found to be 98.4%, the non reduced material is found to be 0.02%, and the impurities were composed only of 4-methylcyclohexancarboxylic acid and cyclohexancarboxylic acid.

Then, a similar hydrogenation is repeated adding 30 g of terephthalic acid and 270 g of water to the recovered catalyzer.

The hydrogenation is repeated up to 70 times using the recovered catalyzer. However, no a significant variation of reaction time, 1,4-CHDA purity or volume of non reduced material, which are indices of hydrogenation activity of the catalyzer, is observed.

The results of the repeated hydrogenation are shown in the following Table 1.

TABLE 1

| Repeated times | Reaction time (minute) | Purity of 1,4-CHDA (%) | Non reduced material (%) |
|---|---|---|---|
| 1 | 50 | 98.4 | 0.02 |
| 10 | 53 | 97.7 | 0.02 |
| 20 | 53 | 97.6 | 0.02 |
| 40 | 55 | 97.7 | 0.01 |
| 70 | 55 | 97.6 | 0.02 |

[Reference example 1] (First step)

The hydrogenation is repeated up to 20 times as in Embodiment example 1 except that a stainless autoclave is used in place of the glass one of the Embodiment example 1.

As the result, the time necessary for the hydrogenation is prolonged and further repetition is abandoned. The results of the repeated hydrogenation are shown in the following Table 2.

TABLE 2

| Repeated times | Reaction time (minute) | Purity of 1,4-CHDA (%) | Non reduced material (%) |
|---|---|---|---|
| 1 | 55 | 98.4 | 0.01 |
| 10 | 75 | 97.1 | 0.01 |
| 20 Abandoned thereafter | 145 | 97.8 | 0.02 |

[Embodiment example 2] (First step)

1.2 kg of terephthalic acid, 4.8 kg of water and 240 g of 10% palladium-carbon catalyzer are introduced into a stainless steel (SUS306) autoclave of 10,000 ml provided with glass lining on the inner wall and the liquid contact portion of the agitator blades. This mixture is hydrogenated at 130° C. under a hydrogen pressure of 8.5 to 9.8 kg/cm$^2$, and the reaction stops after 65 minutes from the beginning of the reaction, when hydrogen absorption is no longer observed.

The reaction liquid is cooled down, evacuated from the autoclave, filtered at 135° C. by an enamel pressure filter of 10 liters, and cooled down. The filtrate is then analyzed to find the 1,4-CHDA purity to be 97.4% and the non reduced material to be 0.02%.

[Embodiment example 3] (First step)

600 g of terephthalic acid, 5.4 kg of water and 120 g of 10% palladium-carbon catalyzer are introduced into the same autoclave as Example 2 and hydrogenated at 140° C. under a hydrogen pressure of 5 to 6 kg/cm$^2$. The reaction stops after 115 minutes from the beginning of the reaction, when hydrogen absorption is no longer observed.

The reaction liquid is cooled down and, as in Example 2, heat filtered, cooled down, and the filtrate is then analyzed to find the 1,4-CHDA purity to be 96.5% and the non reduced material to be 0.03%.

[Embodiment example 4] (First step)

The hydrogenation is carried out as in Example 3 except that 240 g of 7.5% palladium-carbon catalyzer is used, the reaction temperature is 150° C. and the hydrogen pressure is 8.5 to 9.8 kg/cm$^2$. In consequence, the reaction time is 75 minutes from the beginning of the reaction. The analysis shows that the 1,4-CHDA purity is 96.8% and the non reduced material is 0.03%

[Embodiment example 5] (First step)

900 g of terephthalic acid, 5.1 kg of water and 400 g of 5% palladium-carbon catalyzer are introduced into the same autoclave as Example 2 and hydrogenated at 130° C. under a hydrogen pressure of 8.5 to 9.8 kg/cm$^2$. The reaction stops after 65 minutes from the beginning of the reaction, when hydrogen absorption is no longer observed.

The reaction liquid is analyzed as in Example 2 to find the 1,4-CHDA purity to be 98.2% and the non reduced material to be 0.01%.

[Embodiment example 6] (Second step)

A reactor is provided with a heating jacket, as shown in FIG. 1, wherein a stainless steel tower (B) is provided with a jacket and the other portions in contact with liquid are respectively layered with a glass lining. The equipment is supplied and connected to pipings provided with a heating jacket as shown in the drawing.

The dimensions of respective components of tower (A) shall be: vessel (1) (inner diameter: 5 cm, length: 20 cm), column (2) (inner diameter: 5 cm, length: 198.7 cm, capacity: 3900 ml), and liquid receiving vessel (3) (inner diameter: 5 cm, length: 70 cm). The dimensions of tower (B) shall be: vessel (4) (inner diameter: 5 cm, length: 20 cm), column (5) (inner diameter: 5 cm, length: 198.7 cm, capacity: 3900 ml), and liquid receiving vessel (6) (inner diameter: 5 cm, length: 70 cm). Column (2) is filled with ceramic Raschig rings (inner diameter: 3 mm, outer diameter: 6 mm, length: 6 mm), and column (5) is filed with wire gauze of 5 mm×12 mm, respectively.

The towers in FIG. 1 further include: an inlet for solution containing 1,4-CHDA (a) on the top and a steam outlet (b) on the side of the vessel (1); a steam inlet (c) on the side and an outlet port (d) for 1,4-CHDA at the bottom of the liquid receiving vessel (3); an inlet for alkaline aqueous solution (e) on the top and a steam outlet (f) on the side of the vessel (4); and a steam inlet (g) on the side and a evacuation port for alkaline aqueous solution (h) at the bottom of the liquid receiving vessel (6).

First, a steam pressure of 4.8 kg/cm$^2$ is applied to the jacket portion of the equipment, and the temperature in the system is adjusted to 150° C. Then, the steam circulation pump (9) is driven at a flow rate of 57 ml (volume as water) per minute to advance steam to the steam inlet (c) for circulating the steam in the equipment.

Then, the pump (8) is driven to supply 10% aqueous solution of sodium hydroxide to the inlet (e) through a preheater (15) at a flow rate of 67 ml per minute, and the solution containing 1,4-CHDA obtained in Example 2 (concentration of 20% , 1,4-CHDA purity of 97.4%) is supplied by the pump (7) at a flow rate of 133 ml per minute. The respective liquids are evacuated from the drain port (d) and evacuation port (h) of their respective towers every 10 minutes.

One (1) hour and two (2) hours after, the solution containing the produced 1,4-CHDA is extracted from the evacuation port (d) of the liquid receiving vessel (3), analyzed and no purity is found.

[Embodiment example 7] (Second step)

The treatment is performed adopting the same method as Example 6 except for the following parameters.

The temperature in the piping and the equipment is adjusted to 130° C., the solution obtained under the conditions of Example 5 (concentration of 15%, 1,4-CHDA purity of 98.2%) is used as solution containing 1,4-CHDA, the supply rate to the inlet (a) is 266 ml per minute and the supply rate of 10% aqueous solution of sodium hydroxide to the inlet (e) is 67 ml per minute.

The equipment is driven with the steam circulation pump (9) running at the supply rate of 71 ml (as water volume). One (1) hour and two (2) hours after, the solution is extracted from the evacuation port (d) of the liquid receiving vessel (3), analyzed and no purity is found.

[Embodiment example 8] (Second step)

The equipment is operated same as in Example 6 except that the temperature in the equipment of Example 6 is adjusted to 110° C. the solution obtained under the conditions of Example 3 (concentration of 10%, 1,4-CHDA purity of 96.5%) is used as solution containing 1,4-CHDA, the supply rate to the inlet (a) is 200 ml per minute, and 5% alkali aqueous solution is used, and its supply rate to the inlet (e) is 134 ml per minute. The equipment is driven as in Example 6 with the steam circulation pump (9) running at the supply rate of 71 ml (as water volume). One (1) hour and two (2) hours after, the solution is extracted from the evacuation port (d) of the liquid receiving vessel (3), analyzed and no purity is found.

[Embodiment example 9] (Second step)

As the tower (B) of Example 6, a stainless steel vessel (inner diameter: 12 cm, length: 100 cm, capacity: 11300 ml) without filling is adopted, and a check valve is mounted between the steam outlet (b) and the steam inlet (g) for preventing water back flow and for letting the steam flow from the steam outlet (b) to the steam inlet (g).

5000 ml of 20% potassium hydroxide is introduced so that the steam inlet (g) of the vessel (B) will be under the level of the alkali aqueous solution, and the temperature of the whole system is maintained at 130° C.

The solution containing 1,4-CHDA obtained under the conditions of Example 5 (concentration of 15%, 1,4-CHDA purity of 98.2%) is supplied from the inlet (a) at a flow rate of 67 ml per minute, and the equipment was operated as in Example 6 except that the continuous supply and evacuation of alkali is omitted. One (1) hour and two (2) hours after, the solution is extracted from the evacuation port (d) of the liquid receiving vessel (3), analyzed and no purity is found.

[Embodiment example 10] (Second step)

Using only tower (A) of Example 6, a piping is connected to the steam inlet (c) so that steam of the same steam pressure as the outside jacket, a throttle valve and a cooler are attached to the steam outlet (b) so that this structure can condense the evacuated steam.

A steam pressure of 2.0 kg/cm$^2$ is applied to the jacket of the equipment and the piping in order to keep the temperature at 120° C., the steam inlet (c) valve is opened to introduce steam into the equipment and the steam outlet (b) valve is opened so as to adjust the flow rate of the cooled and evacuated condensate at 57 ml per minute.

Then the solution containing 1,4-CHDA obtained under the conditions of Example 4 (concentration of 1,4-CHDA purity of 96.8%) is supplied through the preheater (14) to the inlet (a) at a flow rate of 100 ml per minute by the pump (7), and the steam outlet (c) valve is adjusted so that the concentration of refined solution containing 1,4-CHDA evacuated from the evacuation port (d) will be 10%.

The liquid is evacuated from the evacuation port (d) every 10 minutes, then one (1) hour and two (2) hours after, the extracted liquid is analyzed and no purity is found.

[Embodiment example 11] (Second step)

Figure 2:
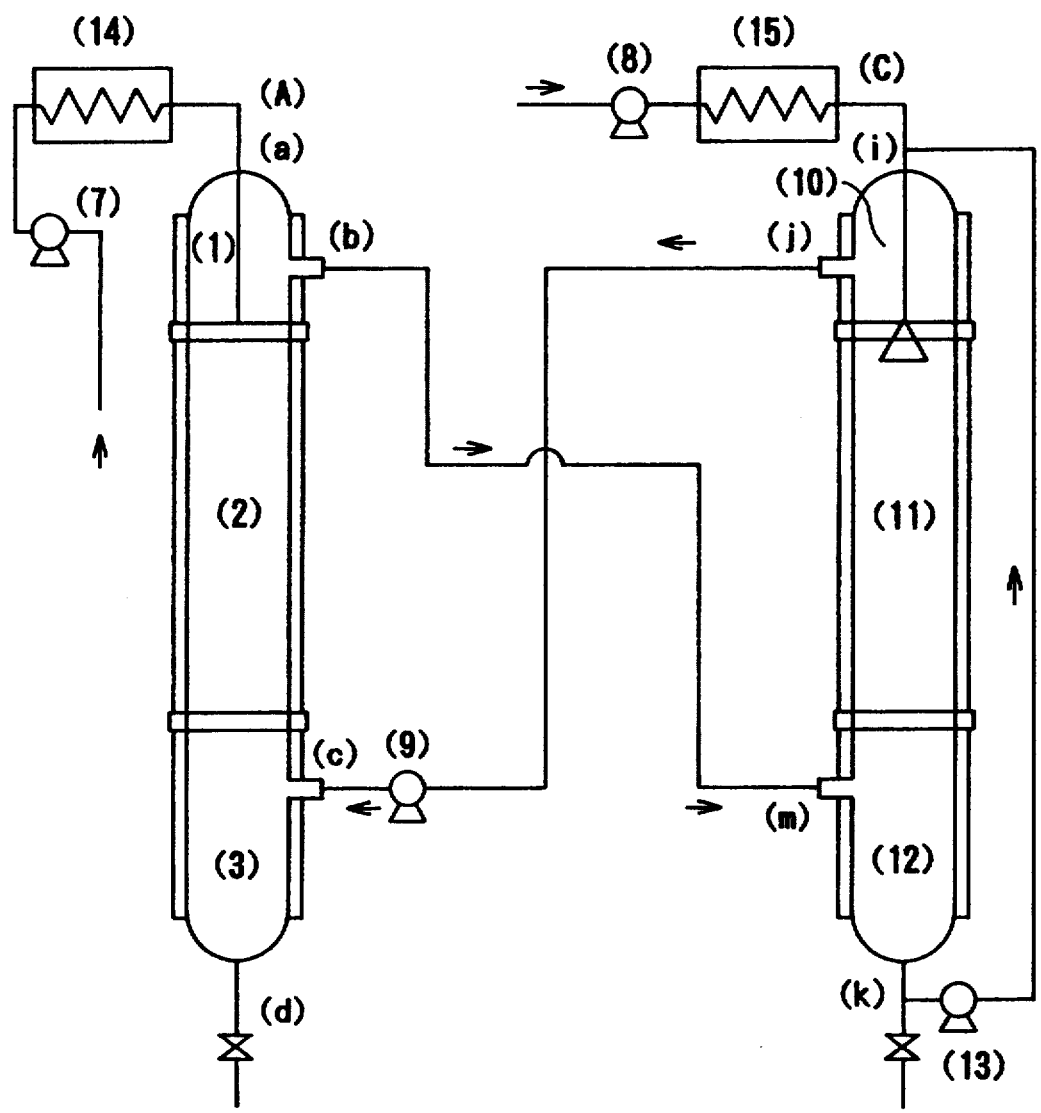
FIG. 2 is a schematic diagram for the second Example of the equipment provided with a heating jacket to be used for an embodiment of the present invention.

As shown in FIG. 2, a tower (C) with a jacket (made of SUS316) is provided in place of tower (B) of Example 6. As in tower (B), the structure of tower (C) comprises a vessel (10) (inner diameter: 17 cm, length: 40 cm), an alkali showering apparatus (11) (inner diameter: 17 cm, length: 99.6 cm, capacity: 22600 ml) and a liquid receiving vessel (12) (inner diameter: 17 cm, length: 49.8 cm, capacity: 11300 ml).

The following devices are attached respectively to tower (C): an alkali liquid inlet (i) on the top and a distributor at the extremity of an alkali pipe of the vessel (10) so that this structure permits the alkali liquid introduced from the alkali liquid inlet (i) to disperse uniformly in the form of shower in the alkali showering apparatus (11). Additionally, a steam outlet (j) is attached on the side and a throttle valve and a cooler are attached on the outside of the vessel (10).

A liquid outlet port (k) is attached at the bottom and a steam inlet (m) and a valve are attached on the side of the liquid receiving vessel (12). A pump (13) is mounted between the inlet of alkaline liquid inlet (i) and the liquid outlet port (k) so that this structure permits the liquid to circulate toward the alkali liquid inlet (i).

Moreover, the steam outlet (b) and the steam inlet (m), the steam inlet (c) and the steam outlet (j) are respectively connected by piping, and a steam circulation pump (9) is mounted between the steam inlet (c) and the steam outlet (j) so that steam circulates toward the steam inlet (c).

First, 5000 ml of 10% solution of sodium hydroxide is introduced in the vessel (10) of the tower (C), a steam pressure of 2 kg/cm$^2$ is applied to each jacket and the temperature is adjusted to 120° C. Then, the pump (13) is driven to circulate at a speed of 6000 ml per minute, and the steam circulation pump (9) is driven at a flow rate of 71 ml (volume as water) per minute. At the same time, the solution containing 1,4-CHDA obtained under the parameters of Example 5 is supplied to the inlet (a) of the tower (A) at a flow rate of 266 ml per minute, and the solution containing 1,4-CHDA is evacuated from the liquid outlet port (d) every 10 minutes.

One (1) hour and two (2) hours after, the quality of the solution extracted from the evacuation port (d) is analyzed and no purity is found.

We claim:

1. A process for preparing 1,4-cyclohexandicarboxylic acid comprising:

a first step of hydrogenating a solution containing terephthalic acid in the presence of a palladium catalyst in a vessel made of at least one acid resistant material selected from the group consisting of: hastelloy steel, inconel steel, ceramics, enamel, glass, and their compacts, or in a vessel layered with at least one of said acid resistant materials or their compacts, to thereby prepare 1,4-cyclohexandicarboxylic acid solution; and a second step of contacting the 1,4-cyclohexandicarboxylic acid solution obtained in the first step with steam, and extracting impurities moved to the steam.

2. A process for preparing 1,4-cyclohexandicarboxylic acid of claim 1, wherein the hydrogenating in the first step is performed under a hydrogen pressure between 2 kg/cm$^2$ and less than 10 kg/cm$^2$.

3. A process for preparing 1,4-cyclohexandicarboxylic acid of claim 1, wherein the hydrogenating in the first step is performed in a pressure vessel provided with a vitreous layer.

4. A process for preparing 1,4-cyclohexandicarboxylic acid of claim 1, wherein in the second step, 1,4-cyclohexandicarboyylic acid is brought continuously into contact in counterflow with steam by continuously supplying 1,4-cyclohexandicarboxylic acid solution to a first end of a packed tower, supplying steam continuously to a second end of the packed tower, evacuating 1,4-cyclohexandicarboxylic acid discontinuously or continuously from the second end of the packed tower, evacuating steam from the first end of the packed tower, and removing impurities from the steam by condensing the steam or by passing the steam through an alkaline aqueous solution.

5. A process for preparing 1,4-cyclohexandicarboxylic acid of claim 2, wherein the hydrogenating in the first step is performed in a pressure vessel provided with a vitreous layer.

6. A process for preparing 1,4-cyclohexandicarboxylic acid of claim 2, wherein in the second step, 1,4-cyclohexandicarboxylic acid is brought continuously into contact in counterflow with steam by continuously supplying 1,4-cyclohexandicarboxylic acid solution to a first end of a packed tower, supplying steam continuously to a second end of the packed tower, evacuating 1,4-cyclohexandicarboxylic acid discontinuously or continuously from the second end of the packed tower, evacuating steam from the first end of the packed tower, and removing impurities from the steam by condensing the steam or by passing the steam through an alkaline aqueous solution.

7. A process for preparing 1,4-cyclohexandicarboxylic acid of claim 3, wherein in the second step, 1,4-cyclohexandicarboxylic acid is brought continuously into contact in counterflow with steam by continuously supplying 1,4-cyclohexandicarboxylic acid solution to a first end of a packed tower, supplying steam continuously to a second end of the packed tower, evacuating 1,4-cyclohexandicarboxylic acid discontinuously or continuously from the second end of the packed tower, evacuating steam from the first end of the packed tower, and removing impurities from the steam by condensing the steam or by passing the steam through an alkaline aqueous solution.

8. A process for preparing 1,4-cyclohexandicarboxylic acid of claim 5, wherein in the second step, 1,4-cyclohexandicarboxylic acid is brought continuously into contact in counterflow with steam by continuously supplying 1,4-cyclohexandicarboxylic acid solution to a first end of a packed tower, supplying steam continuously to a second end of the packed tower, evacuating 1,4-cyclohexandicarboxylic acid discontinuously or continuously from the second end of the packed tower, evacuating steam from the first end of the packed tower, and removing impurities from the steam by condensing the steam or by passing the steam through an alkaline aqueous solution.

9. A process for preparing 1,4-cyclohexandicarboxylic acid of claim 4, further including a step of recycling the steam.

10. A process for preparing 1,4-cyclohexandicarboxylic acid of claim 9, wherein the steam is heated during the recycling step.

11. A process for preparing 1,4-cyclohexandicarboxylic acid of claim 6, further including a step of recycling the steam.

12. A process for preparing 1,4-cyclohexandicarboxylic acid of claim 11, wherein the steam is heated during the recycling step.

13. A process for preparing 1,4-cyclohexandicarboxylic acid of claim 7, further including a step of recycling the steam.

14. A process for preparing 1,4-cyclohexandicarboxylic acid of claim 13, wherein the steam is heated during the recycling step.

15. A process for preparing 1,4-cyclohexandicarboxylic acid of claim 8, further including a step of recycling the steam.

16. A process for preparing 1,4-cyclohexandicarboxylic acid of claim 15, wherein the steam is heated during the recycling step.

17. A process for preparing 1,4-cyclohexandicarboxylic acid of claim 1, wherein the hydrogenating in the first step is performed under a hydrogen pressure between 1 kg/cm$^2$ and 50 kg/cm$^2$.

* * * * *